(12) United States Patent
Sanger

(10) Patent No.: US 11,833,030 B2
(45) Date of Patent: *Dec. 5, 2023

(54) INTRAOCULAR LENS, METHOD FOR DESIGNING THE SAME, AND METHOD FOR MANUFACTURING THE SAME

(71) Applicant: Hoya Corporation, Tokyo (JP)

(72) Inventor: Demas Sanger, Fukaya (JP)

(73) Assignee: Hoya Corporation, Tokyo (JP)

( * ) Notice: Subject to any disclaimer, the term of this patent is extended or adjusted under 35 U.S.C. 154(b) by 76 days.

This patent is subject to a terminal disclaimer.

(21) Appl. No.: 17/558,175

(22) Filed: Dec. 21, 2021

(65) Prior Publication Data

US 2022/0249224 A1  Aug. 11, 2022

Related U.S. Application Data

(63) Continuation of application No. 16/328,133, filed as application No. PCT/JP2017/030653 on Aug. 28, 2017, now Pat. No. 11,234,810.

(30) Foreign Application Priority Data

Aug. 31, 2016  (JP) .................................. 2016-169462

(51) Int. Cl.
  *A61F 2/16*  (2006.01)
(52) U.S. Cl.
  CPC .............. *A61F 2/1654* (2013.01); *A61F 2/16* (2013.01); *A61F 2/1618* (2013.01); *A61F 2/1627* (2013.01); *A61F 2002/1681* (2013.01)
(58) Field of Classification Search
  CPC .... A61F 2/1654; A61F 2/1618; A61F 2/1627; A61F 2002/1681; A61F 2230/0017;
  (Continued)

(56) References Cited

U.S. PATENT DOCUMENTS

| 4,298,994 A | 11/1981 | Clayman |
| 6,926,744 B1 | 8/2005 | Bos et al. |

(Continued)

FOREIGN PATENT DOCUMENTS

| EP | 1618857 A1 | 1/2006 |
| EP | 2805694 A1 | 11/2014 |

(Continued)

OTHER PUBLICATIONS

PCT International Search Report dated Oct. 3, 2017 for PCT App. Ser. No. PCT/JP2017/030653.

(Continued)

*Primary Examiner* — Paul B Prebilic
(74) *Attorney, Agent, or Firm* — Henricks Slavin LLP

(57) ABSTRACT

Provided is an intraocular lens including a lens body having a back surface disposed on a retinal side and a front surface disposed on a corneal side, wherein an entire back surface is shaped in such a way as to protrude from a peripheral edge of the back surface toward the retinal side in a direction of an optical axis, in a shape of a truncated cone, and the front surface has any of the following shapes (i) to (iii);

(i) the front surface is shaped in such a way as to start to be recessed toward the retinal side in the direction of the optical axis when viewed toward a center from a peripheral edge of the front surface, (ii) the front surface is shaped in such a way that an initial part from the peripheral edge of the front surface toward the center is flat, (iii) the front surface is shaped in such a way as to start to protrude toward the corneal side in the direction of the optical axis when viewed toward the center from the peripheral edge of the front surface, but a rate of rise of a protrusion from the peripheral edge of the front (Continued)

surface is smaller than a rate of rise of a protrusion from the peripheral edge of the back surface.

16 Claims, 9 Drawing Sheets

(58) Field of Classification Search
CPC ...... A61F 2230/0067; A61F 2250/0036; A61F 2250/0053
See application file for complete search history.

(56) References Cited

U.S. PATENT DOCUMENTS

| | | | |
|---|---|---|---|
| 11,234,810 B2 | 2/2022 | Demas | |
| 2010/0097569 A1* | 4/2010 | Weeber | G02C 7/06 623/6.3 |
| 2010/0161051 A1* | 6/2010 | Hong | A61F 2/1618 351/159.01 |
| 2011/0130832 A1 | 6/2011 | Shoji et al. | |
| 2014/0067060 A1* | 3/2014 | Wanders | A61F 2/1618 623/6.28 |
| 2014/0358225 A1 | 12/2014 | Wang | |
| 2015/0250583 A1 | 9/2015 | Rosen et al. | |

FOREIGN PATENT DOCUMENTS

| | | | | |
|---|---|---|---|---|
| EP | 2941222 B1 * | 5/2022 | .......... | A61F 2/1618 |
| WO | WO 98/05273 A1 | 2/1998 | | |
| WO | WO 03/055416 A1 | 7/2003 | | |

OTHER PUBLICATIONS

English language translation of PCT International Preliminary Examination Report dated Mar. 14, 2019 for PCT App. Ser. No. PCT/JP2017/030653.
EPO Extended Search Report dated Jul. 16, 2020 for EP App. Ser. No. 17846371.7.

* cited by examiner

FIG. 3
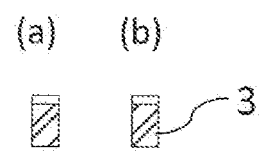
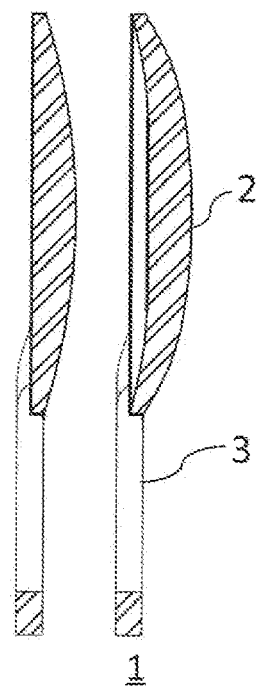

FIG. 6    (a)  (b)
 
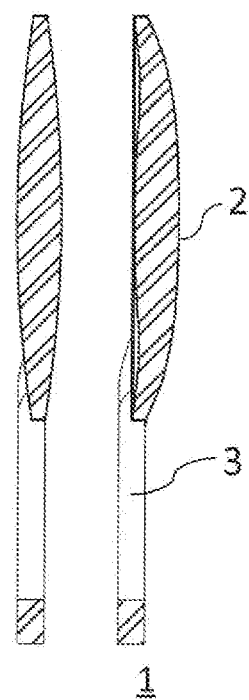

FIG. 7
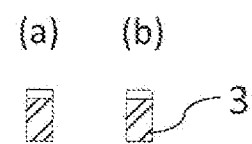
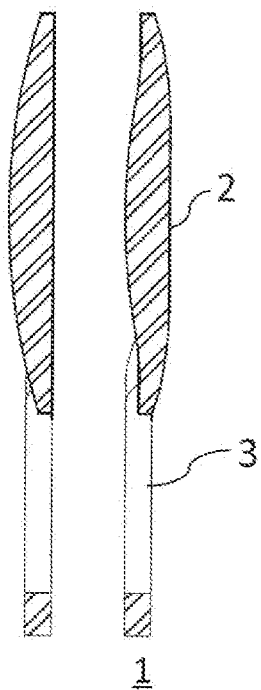

FIG. 8
(a) (b)
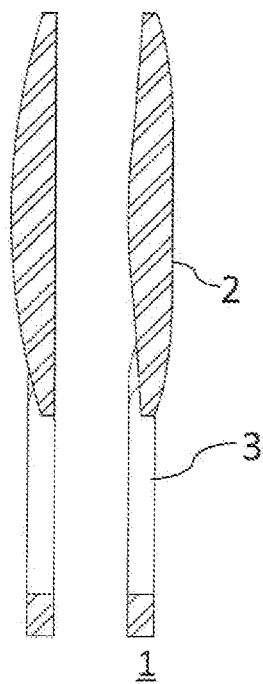

INTRAOCULAR LENS, METHOD FOR DESIGNING THE SAME, AND METHOD FOR MANUFACTURING THE SAME

This application is a continuation of U.S. application Ser. No. 16/328,133, with a 35 U.S.C. 371(d) date of May 11, 2019, now U.S. Pat. No. 11,234,810, which is a U.S. national phase application under 35 U.S.C. § 371 of International Patent Application No. PCT/JP2017/030653 filed Aug. 28, 2017, which claims priority to Japanese patent application No. 2016-169462, filed Aug. 31, 2016.

TECHNICAL FIELD

The present invention relates to an intraocular lens, a method of designing the same, and a method of manufacturing the same.

BACKGROUND ART

An intraocular lens which plays a role in the correction of a visual function after removing a crystal lens opacified by a cataract is known. For example, when a crystal lens is opacified due to a cataract, a recovery of vision is attempted by a surgical procedure which inserts an artificial intraocular lens in a crystalline lens capsule, in place of this opaque crystal lens.

It is required to suppress a secondary cataract after inserting an intraocular lens into the crystalline lens capsule (Patent Document 1). The secondary cataract is a phenomenon in which lens epithelial cells migrate to the posterior of the intraocular lens, i.e., into the gap between the lens body of the intraocular lens and the posterior capsule, which causes fibrosis or swelling and degeneration, and opacifies the posterior capsule of the crystal lens capsule.

Further, it is also required to make a small incision when inserting the intraocular lens into the crystal lens capsule. In order to make the small incision, it is effective to insert the intraocular lens into the crystal lens capsule in a folded state (Patent Document 2).

Furthermore, after the intraocular lens is inserted into the crystal lens capsule, it is also required to stably place the intraocular lens into the crystal lens capsule (i.e., intracapsular stability) (Patent Document 3). The intracapsular stability is required, specifically, in a toric intraocular lens.

CITATION LIST

Patent Document

[Patent Document 1] WO2003/055416
[Patent Document 2] WO2009/153873
[Patent Document 3] Japanese Translation of PCT International Application Publication No. 2015-503977

SUMMARY OF INVENTION

Technical Problem

The present invention makes as its technical subject to provide an intraocular lens for improving the intracapsular stability while facilitating fold of the intraocular lens, and suppressing the occurrence of a secondary cataract, and a related technology thereof.

Solution to Problem

The present inventor examined an approach completely different from the techniques described in Patent Documents 1 to 3. As a result, the configuration of the present invention described hereinafter is achieved.

The first aspect of the present invention is an intraocular lens including a lens body having a back surface disposed on a retinal side and a front surface disposed on a corneal side, wherein an entire back surface is shaped in such a way as to protrude from a peripheral edge of the back surface toward the retinal side in a direction of an optical axis, in a shape of a truncated cone, and, the front surface has any of the following shapes (i) to (iii), (i) the front surface is shaped in such a way as to start to be recessed toward the retinal side in the direction of the optical axis when viewed toward the center from a peripheral edge of the front surface, (ii) the front surface is shaped in such a way that an initial part from the peripheral edge of the front surface toward the center is flat, (iii) the front surface is shaped in such a way as to start to protrude toward the corneal side in the direction of the optical axis when viewed toward the center from the peripheral edge of the front surface, but a rate of rise of a protrusion from the peripheral edge of the front surface is smaller than a rate of rise of a protrusion from the peripheral edge of the back surface.

The second aspect of the present invention is the invention according to the first aspect satisfying at least one of the following conditions, (Condition 1)

in the back surface, a sag value of the back surface at a distance Lp in a region within a predetermined distance from an optical center Cp, to a virtual spherical surface Sp having a curvature radius Rcp at the optical center Cp, (with this optical center Cp as a vertex), is not more than a sag value of the virtual spherical surface Sp at the distance Lp, and a sag value of the back surface at a distance lp outside of the region within the predetermined distance becomes larger than a sag value of the virtual spherical surface Sp at the distance lp, and in the front surface, a sag value of the front surface at a distance La in a region within a predetermined distance from an optical center Ca, to a virtual spherical surface Sa having a curvature radius Rca at the optical center Ca, with this optical center Ca as a vertex, is not less than a sag value of the virtual spherical surface Sa at the distance La, and a sag value of the front surface at a distance la outside of the region within the predetermined distance becomes smaller than a sag value of the virtual spherical surface Sa at the distance la, (Condition 2)

in the back surface, a sag average value of the back surface in a region within a predetermined distance from an optical center Cp is not more than a sag average value of the virtual spherical surface Sp in the region within the predetermined distance, and a sag average value of the back surface outside of the region within the predetermined distance becomes larger than a sag average value of the virtual spherical surface Sp outside of the region within the predetermined distance, and in the front surface, a sag average value of the front surface in a region within a predetermined distance from an optical center Ca is not less than a sag average value of the virtual spherical surface Sa inside of the region within the predetermined distance, and a sag average value of the front surface outside of the region within the predetermined distance becomes smaller than a sag average value of the virtual spherical surface Sa outside of the region within the predetermined distance, (Condition 3)

in the back surface and the front surface, when the sag values thereof are measured at a predetermined number of measurement points equally spaced from each other, there are half or more measurement points which satisfy Condition 1, inside and outside of the region within the predetermined distance, wherein the sag value is a vertical distance from a tangent plane at the optical center, to the virtual spherical surface, distances Lp, lp, La and la are the distances from the optical center when viewed in parallel to the tangent plane, the sag average value of the back surface or the virtual spherical surface Sp is the average value of the sag value at each point inside or outside of the region within the predetermined distance from the optical center Cp, and the sag average value of the front surface or the virtual spherical surface Sa is the average value of the sag value at each point inside or outside of the region within the predetermined distance from the optical center Ca.

The third aspect of the present invention is the invention according to the second aspect, wherein a peripheral position Ep of the back surface is separated by 0.1 mm or more from a peripheral position Eps of the virtual spherical surface Sp in a direction vertical to a tangent plane at the optical center Cp, namely, in a direction from the back surface to the front surface, the peripheral position Eps being located at a distance of a peripheral edge Ep of the back surface from the optical center Cp on the tangent plane, and a peripheral position Ea of the front surface is separated by 0.1 mm or more from a peripheral position Eas of the virtual spherical surface Sa in a direction vertical to a tangent plane at an optical center Ca, namely, in a direction from the back surface to the front surface, the peripheral position Eas being located at a distance of a peripheral edge Ea of the front surface from the optical center Ca on the tangent plane.

The fourth aspect of the present invention is the invention according to the second or third aspect, wherein an optical function in accordance with a prescription is exhibited in an entire lens body.

The fifth aspect of the present invention is the invention according to the second or third aspect, wherein the back surface and the front surface of the lens body respectively include an effective optical portion which exhibits an optical function in accordance with a prescription and a peripheral portion disposed around the effective optical portion.

The sixth aspect of the present invention is the invention according to any one of the first to the fifth aspects, wherein the front surface, the back surface, or both surfaces of the lens body is spherical, aspheric, or a combination thereof.

The seventh aspect of the present invention is the invention according to any one of the first to the sixth aspects, wherein the front surface, the back surface, or both surfaces of the lens body have a shape which is at least one of monofocal, bifocal or multifocal, or tonic, the bifocal and the multifocal being refractive, diffractive, or a combination thereof.

The eighth aspect of the present invention is the invention according to any one of the first to the seventh aspects, further including:

a support portion extending from the lens body.

The ninth aspect of the present invention is a method of designing an intraocular lens including a lens body, wherein the lens body has a front surface disposed on a corneal side and a back surface disposed on a retinal side, the method including:

step 1 of changing a design of a center portion of the back surface and a center portion of the front surface of the lens body so as to be moved by a predetermined distance to the retinal side in a direction of an optical axis, the lens body being designed according to a prescription, and continuously to step 1, step 2 of changing a design of a peripheral portion disposed around the center portion of the back surface so as to satisfy the prescription and so that an entire back surface is shaped in such a way as to protrude from a peripheral edge of the back surface, in a shape of a truncated cone, and changing a design of a peripheral portion disposed around the center portion of the front surface so as to satisfy the prescription and satisfy one of the following (i) to (iii), (i) a peripheral portion of the front surface is shaped in such a way as to start to be recessed toward the retinal side in the direction of the optical axis when viewed toward the center from the peripheral edge of the front surface, (ii) the peripheral portion of the front surface is shaped in such a way that an initial part from the peripheral edge of the front surface toward the center is flat, (iii) the peripheral portion of the front surface is shaped in such a way as to start to protrude from the peripheral edge of the front surface toward the corneal side in the direction of the optical axis when viewed toward the center from the peripheral edge of the front surface, but, a rate of rise of the protrusion from the peripheral edge of the front surface is smaller than a rate of rise of the protrusion from the peripheral edge of the back surface.

The tenth aspect of the present invention is the invention according to the ninth aspect which is the method of designing an intraocular lens including a lens body, wherein the lens body has the front surface disposed on the corneal side and the back surface disposed on the retinal side, the method including:

step 2 of changing a design of the peripheral portion disposed around the center portion of the back surface and the peripheral portion disposed around the center portion of the front surface in order to satisfy at least one of the following conditions, (Condition 1)

in the back surface, a sag value of the back surface at a distance Lp in a region within a predetermined distance from an optical center Cp, to a virtual spherical surface Sp having a curvature radius Rcp at the optical center Cp, with this optical center Cp as a vertex is not more than a sag value of the virtual spherical surface Sp at a distance Lp, and a sag value of the back surface at a distance lp outside of a region within the predetermined distance, becomes larger than a sag value of the virtual spherical surface Sp at the distance lp, and in the front surface, a sag value of the front surface at a distance La in a region within a predetermined distance from an optical center Ca, to a virtual spherical surface Sa having a curvature radius Rca at the optical center Ca, with this optical center Ca as a vertex is not less than a sag value of the virtual spherical surface Sa at the distance La, and a sag value of the front surface at a distance la outside of the region within the predetermined distance becomes smaller than a sag value of the virtual spherical surface Sa at the distance la, (Condition 2)

in the back surface, a sag average value of the back surface in the region within a predetermined distance from the optical center Cp is not more than a sag average value of the virtual spherical surface Sp in the region within the predetermined distance, and a sag average value of the back surface outside of the region within the predetermined distance becomes larger than a sag average value of the virtual spherical surface Sp outside of the region within the predetermined distance, and in the front surface, a sag average value of the front surface in the region within the predetermined distance from the optical center Ca is not less than a sag average value of the virtual spherical surface Sa inside of the region within the predetermined distance, and a sag average value of the front surface outside of the region within the predetermined distance becomes smaller than a sag average value of the virtual spherical surface Sa outside of the region within the predetermined distance, (Condition 3)

in the back surface and the front surface, when the sag values thereof are measured at a predetermined number of measurement points equally spaced from each other, there are half or more measurement points which satisfy Condition 1 inside and outside the region within the predetermined distance.

Note that, the sag value is a vertical distance from the tangent plane at the optical center, to the virtual spherical surface, the distances Lp, lp, La and la are the distances from the optical center when viewed in parallel to the tangent plane, the sag average value of the back surface or the virtual spherical surface Sp is the average value of the sag value at each point inside or outside of the region within the predetermined distance from the optical center Cp, and the sag average value of the front surface or the virtual spherical surface Sa is the average value of the sag value at each point inside or outside of the region within the predetermined distance from the optical center Ca.

The eleventh aspect of the present invention is a method of manufacturing of an intraocular lens, including:

a step of manufacturing the lens body designed by the method of designing according to the ninth or the tenth aspect.

Further, other aspects of the present invention are exemplified as follows.

An intraocular lens including a lens body having two opposing surfaces A and B, wherein an entire surface A is shaped in such a way as to protrude from the peripheral edge of the surface A in a shape of a truncated cone and an entire surface B has a shape which is recessed from the peripheral edge of the surface B, toward one of the directions of the optical axis.

An intraocular lens including at least one part of the front surface having a shape which is recessed (preferably, the entire the front surface is recessed in a shape of a truncated cone) more than the peripheral edge of the front surface.

An intraocular lens including a lens body having the front surface disposed on the corneal side and the back surface disposed on the retinal side, wherein the lens body, viewed from the peripheral edge of the lens body, has a shape which is bent toward the retinal side in the direction of the optical axis.

Note that, with regards to surface B or the front surface, the definition relating to the front surface in the above described Condition 1 may be adopted.

Further, the second aspect of the present invention may be an aspect of an independent invention which is not dependent upon the invention according to the first aspect. Similarly, the tenth aspect of the present invention may be an aspect of an independent invention which is not dependent upon the invention according to the ninth embodiment.

Advantageous Effects of Invention

According to the present invention, the intraocular lens is provided, which improves intracapsular stability and suppresses the occurrence of the secondary cataract while facilitating fold of the intraocular lens.

BRIEF DESCRIPTION OF DRAWINGS

FIG. 3 is a schematic cross-sectional side view illustrating the lens body of the present embodiment, wherein (a) illustrates a lens body in which the back surface is a convex surface and a front surface is a flat surface according to a conventional art, and meanwhile (b) illustrates a state after a change in design (corresponding to (i)) is performed to the back surface and the front surface according to the present embodiment.

FIG. 6 is a schematic cross-sectional side view illustrating another aspect of the lens body, wherein (a) illustrates the lens body in which the back surface and the front surface are convex surfaces according to a conventional art, and (b) illustrates the state after a change in design (corresponding to (i)) is performed to the back surface and the front surface according to the present embodiment.

FIG. 7 is a schematic cross-sectional side view illustrating another embodiment of the lens body, wherein (a) illustrates a lens body in which the back surface is a flat surface and the front surface is a convex surface according to a conventional art, and (b) illustrates a state after a change in design (corresponding to (i)) is performed to the back surface and the front surface according to the present embodiment.

FIG. 8 is a schematic cross-sectional side view illustrating another embodiment of the lens body, wherein (a) illustrates a lens body in which the back surface is a flat surface and the front surface is a convex surface according to a conventional art, and (b) illustrates a state after a change in design (corresponding to (iii)) is performed to the back surface and the front surface according to the present embodiment.

DETAILED DESCRIPTION OF EMBODIMENTS

The embodiments of the present invention will be described in detail hereafter, with reference to the drawings.

In the present embodiment, the explanation is performed in the following order.
1. Method of designing and method of manufacturing the intraocular lens
2. Intraocular lens
   2-1. Lens body
      2-1-1. Back surface
      2-1-2. Front surface
   2-2. Support portion
   2-3. Modified examples or preferred examples relating to the intraocular lens
3. Effect of the embodiment
4. Other modified examples Note that, regarding configurations not described below, a known configuration may be appropriately adopted. Specifically, the contents (particularly the support portion) described in the reference (WO2009/153873) disclosed by the present applicant may be applied to the present embodiment.

Further, the term "to" in the description indicates a value greater than or equal to a predetermined value and less than or equal to a predetermined value.

Further, the lens body of the intraocular lens taken up in the description has two surfaces opposing each other. When the intraocular lens is inserted into the crystal lens capsule, the surface of the lens body on the side contacting with the posterior capsule may be referred to as the back surface, the surface on the retinal side, or the surface on the retinal side in the direction of the optical axis, but the "back surface" is mainly used in the description. Moreover, it is possible to refer to the other surface as the front surface, the surface on the corneal side, or the surface on the corneal side in the direction of the optical axis, but the "front surface" is mainly used in the description. Further, the optical axis direction is also a lens thickness direction, and is a direction from the back surface toward the front surface or vice versa.

1. METHOD OF DESIGNING AND METHOD OF MANUFACTURING THE INTRAOCULAR LENS

Figure 1:
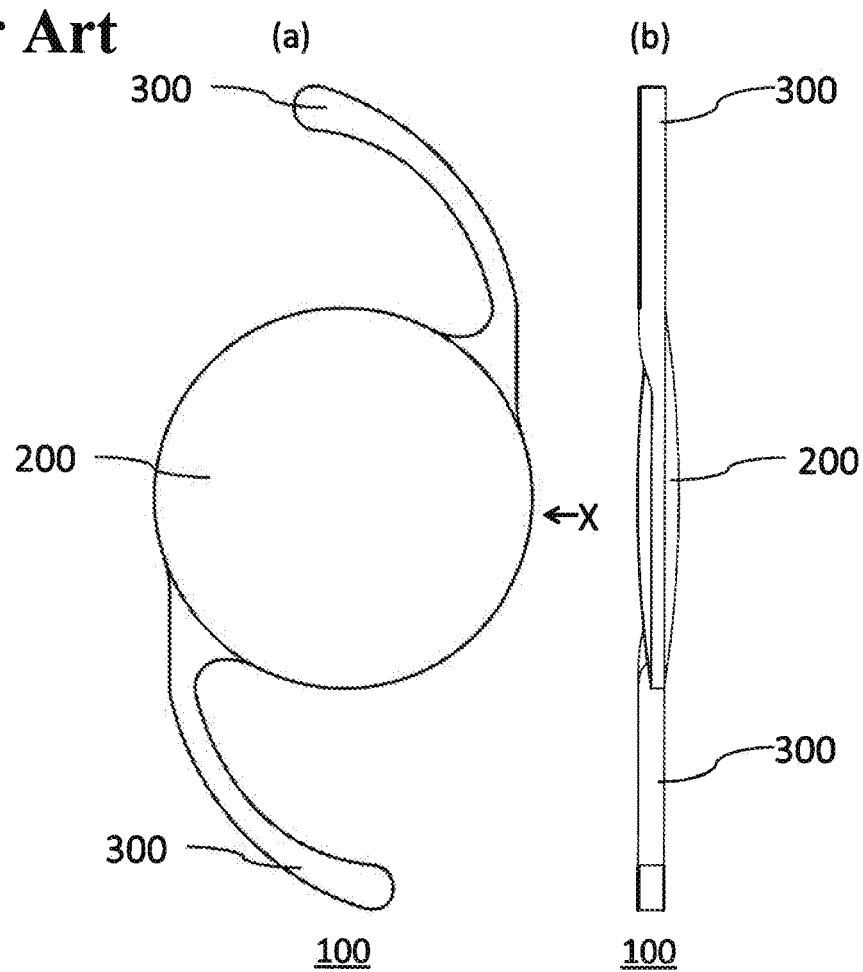
FIG. 1 is a schematic view illustrating a conventional intraocular lens, wherein (a) is a plan view, and (b) is a side view viewed from an arrow x.

First, the intraocular lens in the present embodiment includes a lens body having a lens function and support portions for supporting the lens body in the crystal lens capsule in the same manner as a conventional intraocular lens. FIG. 1 is a schematic view illustrating a conventional intraocular lens, wherein (a) is a plan view and (b) is a side view viewed from an arrow X. Note that, reference numeral 100 indicates a conventional intraocular lens, reference numeral 200 indicates a conventional lens body, and reference numeral 300 indicates a conventional support portion, but hereinafter, these reference numerals will be omitted.

Figure 2:
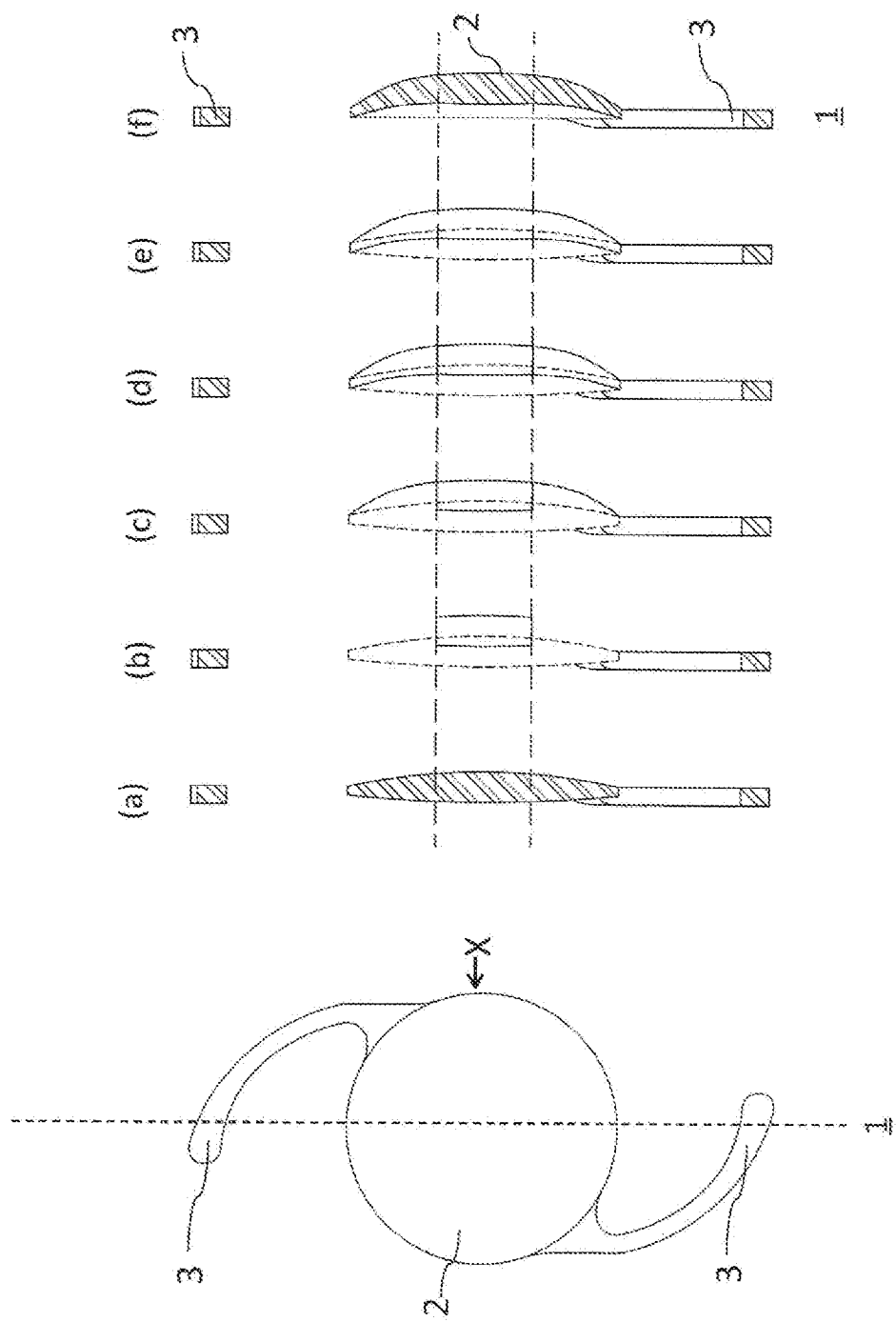
FIG. 2 is a schematic plan view and a schematic cross-sectional side views (a) to (f), where views (b) to (e) are partial section views, illustrating a method of designing and a method of manufacturing the intraocular lens according to the present embodiment.

The method of designing and the method of manufacturing the intraocular lens in the present embodiment are mainly constituted by the following steps. Each step (specifically, regarding two design changing steps described later) is described using FIG. 2. Note that, reference numeral 1 indicates the intraocular lens of the present embodiment, reference numeral 2 indicates the lens body of the present embodiment, and reference numeral 3 indicates the support portion of the present embodiment, but hereinafter, these reference numerals will be omitted.

(Design)

First, the lens body is designed in accordance with a prescription. A known technique may be used as the specific design technique. Note that, a design at this stage is that the back surface as described above does not protrude in a shape of a truncated cone (FIG. 2(a)).

(Change in Design 1)

This step (Step 1) and the subsequent step (Step 2) are one of the major features of the present embodiment. In the step, the center portion of the back surface and the center portion of the front surface of the lens body designed according to the prescription are changed in design so as to move (shift) by a predetermined distance to the retinal side in the direction of the optical axis (FIG. 2(b)).

A movement distance at this time can be arbitrarily set by a designer. For example, if it is desired to further push the center portion of the back surface to the posterior capsule of the crystal lens capsule, the movement distance may be comparatively large (for example, 0.2 to 0.7 mm).

(Change in Design 2)

Following Step 1, in this Step, the back surface is changed in design as follows (FIG. 2(c)).

The peripheral portion disposed around the center portion of the back surface is changed in design so as to satisfy the prescription and so that the entire back surface is shaped in such a way as to protrude from the peripheral edge of the back surface in a shape of a truncated cone.

In the present embodiment, the center portion of the back surface and the center portion of the front surface of a conventional lens body designed in accordance with the prescription (FIG. 2(a)) move (shift) by a predetermined distance to the retinal side in the direction of the optical axis (FIG. 2(b)), and, there is a reason that the back surface of the lens body is formed into the aforementioned shape (FIG. 2(c)). This reason is described below.

The present embodiment adopts a configuration in which the center portion protrudes from the peripheral edge of the back surface of the lens body, by a portion (the peripheral portion) outside of the region within a predetermined distance from an optical center of the back surface. At this time, the peripheral portion surrounding the center portion of the back surface is configured to connect the peripheral edge of the back surface and the center portion. In short, in the present embodiment, the back surface of the lens body is changed in design so as to protrude in a shape of a truncated cone, the truncated cone corresponds to the peripheral portion, and a plateau surface of the truncated cone corresponds to the center portion.

Note that, in the present embodiment, the center portion indicates a center region within a region of a predetermined distance and including the optical center, the peripheral portion indicates an annular region present on the periphery thereof, and the peripheral edge indicates an outermost edge of the lens body (the back surface or the front surface). In short, the front surface and the back surface of the lens body are respectively oriented from the optical center to the peripheral edge, and are present in the order of the center portion, the peripheral portion, and the peripheral edge.

Further, "the entire back surface is shaped in such a way as to protrude from the peripheral edge of the back surface, in a shape of a truncated cone" stated herein refers to the following states.

When the lens body is viewed in a cross-section so as to pass through the optical center, all of the portions of the back surface from the peripheral edge toward the center portion are disposed on the retinal side in the optical axis direction, compared to the peripheral edge of one side (for example, upper side of FIG. 2(f)) of the back surface, and, When the lens body is viewed in a cross-section so as to pass through the optical center, the center portion has a shape of a flat surface of a plateau viewed in a cross-section (shape close to a perpendicular line in the direction of the optical axis), compared to the peripheral portion.

By utilizing such a configuration, when the intraocular lens is inserted into the crystal lens capsule, the center portion in the back surface protrudes so as to become a plateau surface, the posterior capsule is stretched by the center portion and the center portion is strongly pressed against the posterior capsule, and thus, the intracapsular stability improves. As a result, the entry of migratory cells between the posterior capsule and the lens body can be effectively suppressed, which can suppress the occurrence of a secondary cataract.

On the other hand, as shown in FIGS. 2(a) to (e), even after finally being subjected to all of the changes in design in the present embodiment, it is necessary that the peripheral thickness of the lens body (i.e., the distance between the peripheral edge of the back surface and the peripheral edge of the front surface) itself be remained relatively thin.

In this state, the peripheral portion of the back surface is shaped in such a way as to protrude from the peripheral edge toward the center portion as stated above. This shape is defined, for example, by the above description regarding the back surface back surface.

At the same time, the front surface is changed in design so that the peripheral portion disposed around the center portion of the front surface satisfies any of the following (i) to (iii) while satisfying the prescription.

(i) The peripheral portion of the front surface is shaped in such a way as to start to be recessed toward the retinal side in the direction of the optical axis when viewed toward the center from the peripheral edge of the front surface.

(ii) The peripheral portion of the front surface is shaped in such a way that an initial part from the peripheral edge of the front surface toward the center is flat.

(iii) The peripheral portion of the front surface is shaped in such a way as to start to protrude from the peripheral edge of the front surface toward the corneal side in the direction of the optical axis when viewed toward the center, but, the rate of rise of the protrusion from the peripheral edge of the front surface is smaller than the rate of rise of the protrusion from the peripheral edge of the back surface.

Note that, FIG. 2(d) illustrates the case of (i), and FIG. 8(b) which is described later illustrates the case of (iii).

Further, why the front surface of the lens body in the present embodiment is made into the aforementioned shape is as follows.

As stated above, if the center portion of the back surface is configured to be the plateau surface of the truncated cone, the center portion of the back surface certainly presses the posterior capsule strongly.

On the other hand, it is a matter of course that there is a need to achieve the prescription of the intraocular lens. Therefore, there is a need to design the front surface to be close to a diopter which is set prior to the aforementioned Step 1, i.e., prior to the change in design. However, in addition thereto, as stated in the problem of the present invention, there is also a need to realize a thickness of the lens body that facilitates fold of the intraocular lens.

Therefore, in the present embodiment, the front surface is also changed in design in order to satisfy the prescription of the intraocular lens, while the peripheral portion disposed in the periphery of the center portion of the front surface is changed in design in order to satisfy any of the aforementioned (i) to (iii) while satisfying the prescription.

Note that, the portion "shaped in such a way as to start to be recessed" in the aforementioned (i) is an arbitrary portion when viewed toward the center from the peripheral edge of the peripheral portion of the front surface, but for example, it may be assumed to be a portion of 1 to 2 mm from the peripheral edge toward the center, and of course, it may be assumed to be a wider portion (for example, the entire peripheral portion). The same may be applied to the "initial part from the peripheral edge of the front surface toward the center" of (ii), and to the portion "shaped in such a way as to start to protrude" of (iii).

By the way, FIG. 3 is a schematic cross-sectional side view illustrating an aspect of the lens body, wherein (a) illustrates a lens body in which the back surface is a convex surface and a front surface is a flat surface according to a conventional art, and meanwhile (b) illustrates a state after a change in design (corresponding to (i)) is performed to the back surface and the front surface according to the present embodiment.

Further, in the aforementioned (ii), "an initial part from the peripheral edge of the front surface toward the center is flat" means that the initial part from the peripheral edge of the front surface and the peripheral edge toward the center are both present on the vertical plane in the direction of the optical axis. In other words, the description means that there are no protrusions or recesses in the initial part from the peripheral edge of the front surface toward the center.

Further, in the aforementioned (iii), while the front surface is permitted to protrude from the peripheral edge, the protrusion is limited so that "the rate of rise of the protrusion from the peripheral edge of the front surface is smaller than the rate of rise of the protrusion from the peripheral edge of the back surface". The meaning of this limitation will be described using FIG. 8 and FIG. 9.

FIG. 8 is a schematic cross-sectional side view illustrating another embodiment of the lens body, wherein (a) illustrates a lens body in which the back surface is a flat surface and the front surface is a convex surface according to a conventional art, and (b) illustrates a state after a change in design (corresponding to (iii)) is performed to the back surface and the front surface according to the present embodiment.

Figure 9:
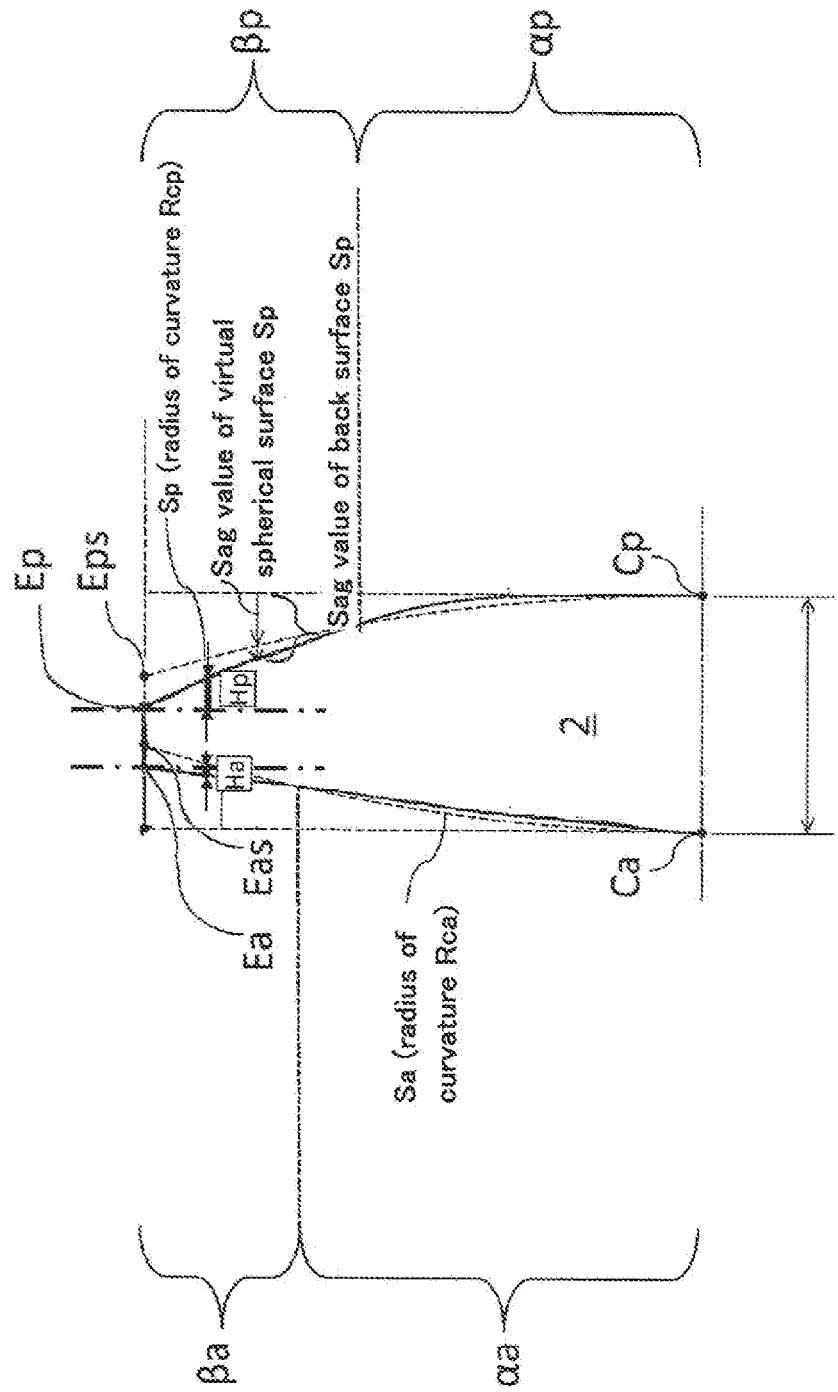
FIG. 9 is a schematic view in the vicinity of the peripheral edge of the lens body after a change in design (iii) is performed to the lens body of the conventional art of FIG. 6(a) in which the back surface and the front surface are convex surfaces.

FIG. 9 is a schematic view in the vicinity of the peripheral edge of the lens body after a change in design (iii) is performed to the lens body of the conventional art of FIG. 6(a) in which the back surface and the front surface are convex surfaces. Note that, the meaning of each undefined reference numeral will be clarified later and will be omitted at this point.

As illustrated in 8(b) and FIG. 9 (specifically, as illustrated in FIG. 9), when viewed toward the center from the peripheral edge Ep of the back surface, distance Hp from a vertical plane (a surface vertical to the direction of the optical axis (Ca-Cp). Long dash line in FIG. 9) to the back surface passing through the peripheral edge Ep of the back surface is set as a rate of rise of the protrusion from the peripheral edge Ep of the back surface in this specification. Similarly, distance Ha from the vertical plane to the front surface passing through the peripheral edge of the front surface Ea is set as a rate of rise of the protrusion from the peripheral edge of the front surface Ea. In short, in the aforementioned (iii), while both the back surface and the front surface are protruded, Ha<Hp is satisfied at the start of the protrusion, and the degree of the rate of rise of the protrusion of the back surface (and thus, the degree of the protrusion) is set higher than that of the front surface, to thereby control a thickness of the peripheral edge of the lens body.

By performing the change in design in each of the aforementioned steps in order to satisfy any of the aforementioned (i) to (iii), it is possible to obtain the lens body with its peripheral thickness itself remaining relatively thin. As a result, it is possible to facilitate fold of the intraocular lens small in an injector used to inject the intraocular lens into the crystal lens capsule.

Then, if necessary, a smoothing process is performed to the center portion and the peripheral portion of the back surface, and the center portion and the peripheral portion of the front surface (FIG. 2(e)). This specific technique of change in design can easily be contrived by a person skilled in the art using well-known software (for example, Optic Studio manufactured by Zemax LLC).

Note that, an example embodying the aforementioned respective definitions will be Conditions 1 to 3 which are described later in <2. Intraocular lens>.

For example, a method of designing the intraocular lens according to the present embodiment includes the aforementioned each step. Note that, the aforementioned technique is a relatively simplified technique, and it is of course acceptable to add known contents other than the above contents.

The method of manufacturing the intraocular lens includes the following steps.

(Manufacture)

After passing through step 1 and step 2 of changing in design as described above, the lens body is manufactured based final design data (FIG. 2(f)). The manufacturing technique is not specifically limited, and any known technique may be used.

2. INTRAOCULAR LENS

The lens body of the present embodiment is achieved based on a novel design concept described above. Therefore, the lens body in the present embodiment also has great features as follows.

"There is provided an intraocular lens including a lens body having a back surface disposed on a retinal side and a front surface disposed on a corneal side, wherein
- an entire back surface is shaped in such a way as to protrude from a peripheral edge of the back surface toward a retinal side in a direction of an optical axis, in a shape of a truncated cone toward the retinal side, and, the front surface has any of the following shapes (i) to (iii),
- (i) the front surface is shaped in such a way as to start to be recessed toward the retinal side in the direction of the optical axis when viewed toward the center from the peripheral edge of the front surface,
- (ii) the front surface is shape in such a way that an initial part from the peripheral edge of the front surface toward the center is flat,
- (iii) the front surface is shaped in such a way as to start to protrude toward the corneal side in the direction of the optical axis when viewed toward the center from the peripheral edge of the front surface, but a rate of rise of the protrusion from the peripheral edge of the front surface is smaller than a rate of rise of the protrusion from the peripheral edge of the back surface."

The example described hereafter is a specific example which reflects a design concept of <1. Method of designing and method of manufacturing the intraocular lens>.

Figure 4:
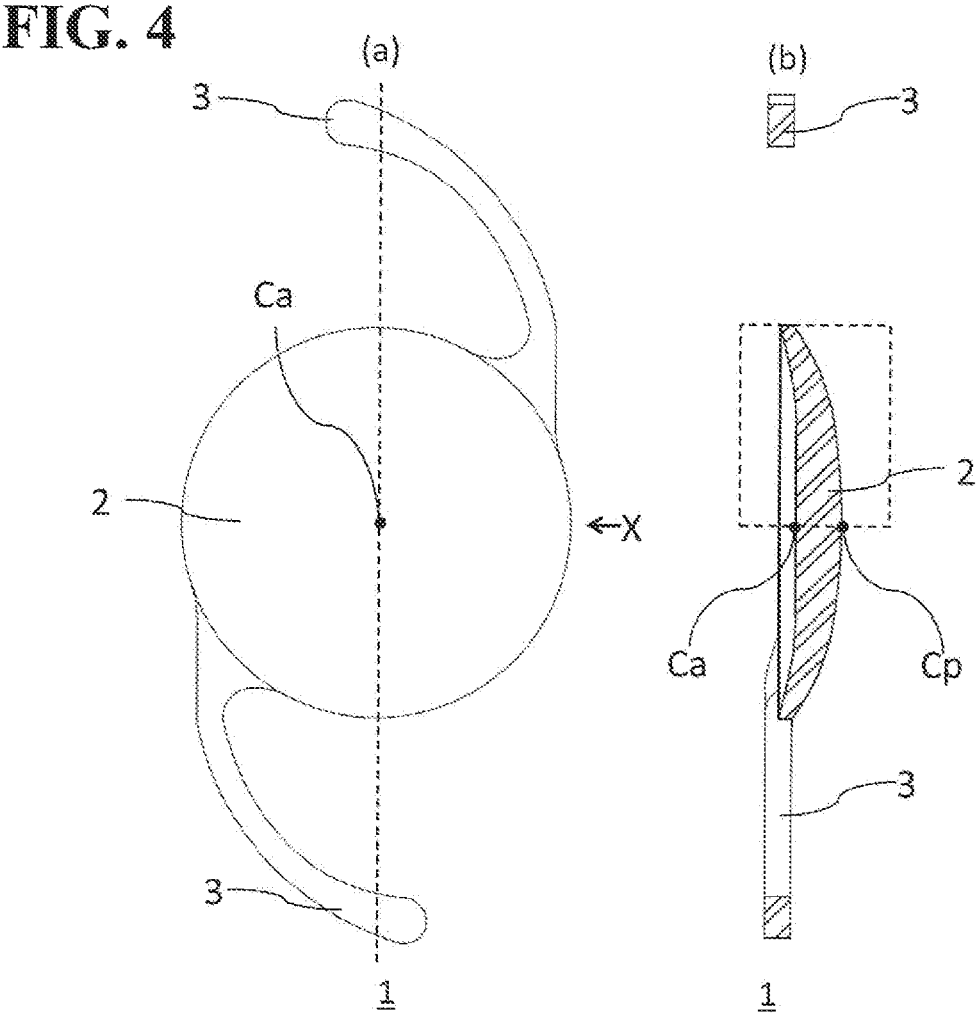
FIG. 4 is a schematic view illustrating the intraocular lens of the present embodiment, wherein (a) is a plan view, and (b) is a cross-sectional side view of a cross section taken along a straight broken line viewed from arrow X.
Figure 5:
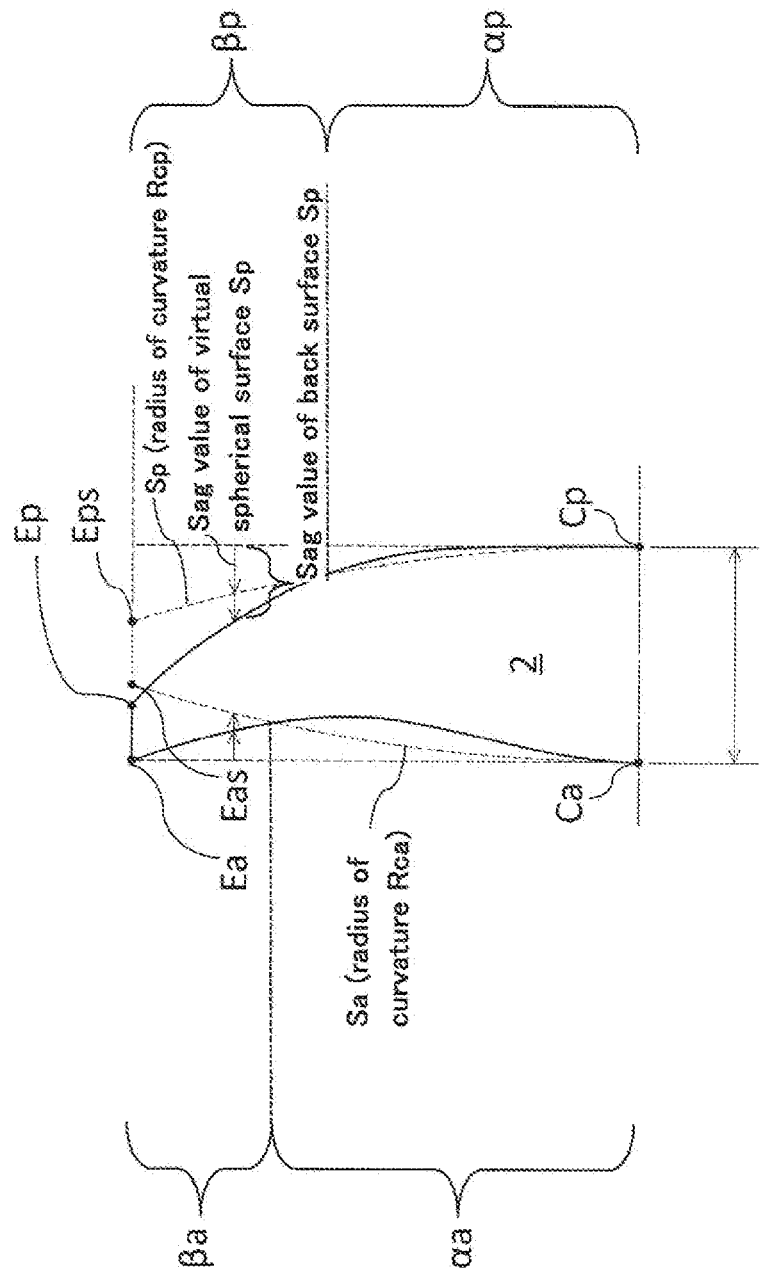
FIG. 5 is a schematic view of a portion surrounded by the broken line of FIG. 4.

The lens body is focused upon and is described hereafter, using FIG. 4 and FIG. 5. FIG. 4 is a schematic view illustrating the intraocular lens of the present embodiment, wherein (a) is a plan view, and (b) is a side sectional view of a cross section taken along the straight broken line viewed from the arrow X. FIG. 5 is a schematic view of a portion surrounded by the broken line of FIG. 4.

2-1. Lens body

The lens body is a relatively soft portion having, for example, a lens function, and is formed in a circular convex lens shape in a plan view. Further, as stated above, the lens body has the front surface disposed on the corneal side and the back surface disposed on the retinal side.

2-1-1. Back Surface

In the present embodiment, the shape of the back surface of the lens body satisfies the following conditions.

In the back surface, a sag value of the back surface at a distance Lp in a region αp within a predetermined distance from an optical center Cp, from a virtual spherical surface Sp having a curvature radius Rcp at the optical center Cp, with this optical center Cp as a vertex, is not more than a sag value of the virtual spherical surface Sp at the distance Lp.

On the other hand, a sag value of the back surface at a distance lp in a region βp outside of a predetermined distance becomes larger than the sag value of the virtual spherical surface SP at the distance lp. Put another way, the curvature of the back surface at the peripheral region is greater than the curvature of the back surface at the center region.

Note that, the virtual spherical surface Sp is the virtual spherical surface having the optical center Cp as the vertex. The curvature radius Rcp of the spherical surface may be the curvature radius Rcp at the optical center Cp. However, strictly speaking, as the optical center Cp itself is a point, the curvature radius cannot be measured, thus, the curvature radius in the vicinity (For example, within a range of a 5 μm radius, or within a range of 5 □m or more) of the optical center Cp is used as the Rcp.

Further, the sag value is a vertical distance from a tangent plane at the optical center to the virtual spherical surface Sp set as stated above, and the distances Lp and lp are the distances from the optical center when viewed parallel to the tangent plane.

Further, the region αp at a predetermined distance means a circular region in a plan view centered at the optical center, and the region βp outside of a predetermined distance means an annular region therearound in a plan view.

FIG. 5 illustrates a state in which a cross-sectional shape of the back surface in the lens body in the present embodiment satisfies the aforementioned condition.

First, the region αp (center portion) at a predetermined distance from the optical center Cp is focused upon in FIG. 5. Within this region αp, the sag value of the back surface of the lens body at the distance Lp is always the same or smaller than the sag value of the virtual spherical surface Sp at an arbitrary distance from the optical center Cp.

This means, in short, that in the region αp at a predetermined distance from the optical center Cp, the back surface of an actual lens body is disposed more on the retinal side (rearward) than the virtual spherical surface Sp. FIG. 5 describes a cross-section passing through the optical center, but even if another cross-section passing through the optical center is viewed, the lens body of the present embodiment satisfies the aforementioned conditions.

Next, the region βp outside (peripheral portion) of a predetermined distance is focused upon in FIG. 5. In this region βp, the sag value of the back surface of the lens body at the distance 1p is always larger than the sag value of the virtual spherical surface Sp at an arbitrary distance 1p from the optical center Cp. This means, in short, that in the region βp outside a predetermined distance from the optical center Cp, the back surface of the actual lens body is disposed more on the corneal side (forward) than the virtual spherical surface Sp. In the same manner as above, even if another cross-section passing through the optical center is viewed, the lens body of the present embodiment satisfies the aforementioned conditions.

Note that, it is preferable that the center portion be smoothly connected (as a continuous surface) with the peripheral portion in the connection portion between the center portion and the peripheral portion.

Further, as the position of the connection portion, if r denotes the radius of the lens body, it is preferable that the portion set within a range of r*3/5 to r*4/5 is made as the connection position in terms of a distance from the optical center Cp toward the peripheral edge.

Since the shape of the back surface is configured as stated above, the posterior capsule is strongly pressed by the center portion of the back surface, thus, the entry of the migratory cells between the posterior capsule and the lens body can be efficiently suppressed.

On the other hand, it is necessary to solve the problem regarding the "fold of the intraocular lens" described in the problem of the present invention. In order to solve this problem, the front surface of the lens body is configured as follows.

2-1-2. Front Surface

In the present embodiment, the shape of the front surface of the lens body satisfies the following conditions.

In the front surface, a sag value of the front surface at the distance la in a region αa (center portion) within a predetermined distance from the optical center Ca, from a virtual spherical surface Sa having the curvature radius Rca at an optical center Ca, with this optical center Ca as a vertex, is not less than the sag value of the spherical surface Sa at the distance La.

On the other hand, a sag value of the front surface at a distance la in a region βa outside of the center portion (peripheral portion) becomes smaller than the sag value of the spherical surface Sa at the distance la.

The above conditions are combined with the conditions regarding the back surface and referred to as (Condition 1).

Note that, the virtual spherical surface Sa and the sag value are the same as those of the above description regarding the back surface. For example, the virtual spherical surface Sa in the front surface is a virtual spherical surface having the optical center Ca as a vertex, the sag value of the front surface is a vertical distance from the tangent plane at the optical center Ca to the virtual spherical surface Sa set as stated above, and the distances La and la are the distances from the optical center when viewed parallel to the tangent plane.

FIG. 5 illustrates a state in which the cross-sectional shape of the front surface in the lens body according to the present embodiment satisfies the aforementioned conditions.

In the front surface as well, the range of the region αa (center portion) within a predetermined distance from the optical center Ca is focused upon in FIG. 5, in the same manner as the back surface. In this region αa, the sag value of the front surface of the lens body at the distance La is always the same or larger than the sag value of the virtual spherical surface Sa at an arbitrary distance La from the optical center Ca.

This means that, in short, in the region αa, i.e., in the center portion, the front surface of the actual lens body is disposed more on the retinal side (rearward) than the virtual spherical surface Sa. While FIG. 5 describes a cross-section passing through the optical center, the lens body of the present embodiment satisfies the aforementioned condition even when viewed at another cross-section passing through the optical center.

Next, in the front surface as well, the region βa outside of the region within the predetermined distance, i.e., the peripheral portion is focused upon in FIG. 5, in the same manner as the back surface. In this region βa, the sag value of the front surface of the lens body at the distance la is always smaller than the sag value of the virtual spherical surface Sa at an arbitrary distance la from the optical center Ca. This means that, in short, in the region βa outside of the region within the predetermined distance from the optical center Ca (peripheral portion), the front surface of the actual lens body is disposed more on the corneal side (forward) than the virtual spherical surface Sa. In the same manner as above, the lens body of the present embodiment satisfies the aforementioned conditions even when viewed at another cross-section passing through the optical center.

Since the above configuration is adopted, it is possible to obtain a lens body with its peripheral thickness itself remaining relatively thin.

Note that, in the front surface as well, the center portion may be smoothly connected (as a continuous surface) with the peripheral portion at the connection portion between the center portion and the peripheral portion, in the same manner as the back surface. Further, as the position of the connection portion, if r denotes the radius of the lens body, it is preferable that the portion set within the range of r*3/5 to r*4/5 is made as the connection position in terms of the distance from the optical center Cp toward the peripheral edge.

In this case, the connection position in the front surface may be disposed on the portion of the front surface opposite to the direction of the optical axis (vertical direction and thickness direction) viewed from the connection position in the back surface, but the connection position may be shifted as shown in FIG. 5. To repeat, the present embodiment, back surface shows a configuration in which the back surface is protruded and meanwhile the lens is made thin on the front surface while realizing a predetermined prescription. Therefore, it is not necessary that the connection position in the back surface is opposed to the connection position in the front surface.

Note that, in addition to the aforementioned definition, the shapes of the back surface and the front surface after the change in design are not specifically limited. Similarly, the shapes of the back surface and the front surface prior to the change in design are not specifically limited.

For example, FIG. 6 is a schematic cross-sectional side view illustrating another aspect of the lens body, wherein (a) illustrates the lens body in which the back surface and the front surface are convex surfaces according to a conventional art, and (b) illustrates a state after a change in design (corresponding to (i)) is performed to the back surface and the front surface according to the present embodiment.

Further, FIG. 7 is a schematic cross-sectional side view illustrating another embodiment of the lens body, wherein (a) illustrates a lens body in which the back surface is a flat surface and the front surface is a convex surface according to a conventional art, and (b) illustrates a state after a change in design (corresponding to (i)) is performed to the back surface and the front surface according to the present embodiment.

Further, in FIG. 8, (a) illustrates a lens body in which the back surface is a flat surface and the front surface is a convex surface according to a conventional art, and (b) illustrates a state after a change in design (corresponding to (iii)) is performed to the back surface and the front surface according to the present embodiment.

Therefore, the change in design shown in the present embodiment enables the shape satisfying the aforementioned Condition 1. This is not an exception even in the case of the aforementioned (iii), i.e., the case when both the front surface and the back surface protrude as illustrated in the expanded view of the vicinity of the peripheral edge of the lens body after change in design (iii) of the lens body of the conventional art illustrated in FIG. 6(a) in which the back surface and the front surface are convex surfaces.

However, as illustrated in FIG. 3, if at least a part of the front surface is shaped in such a way as to be recessed (preferably, the entire the front surface is recessed in a truncated cone) more than the peripheral edge of the front surface, it is possible to make the lens body thinner, thus, this is preferable in consideration of facilitating fold of the lens.

In addition, the diameter of the lens body may be set to any size as long as it is a size suitable for inserting the intraocular lens into the crystal lens capsule in an eye. A specific example of setting the size will be described as follows. The diameter D of the lens body may be preferably set to a range of 5 mm to 7 mm, and may be more preferably set to 7 mm. Since a lens body with a relatively large diameter is used when fixing the intraocular lens in the eye, an influence of eccentric tilting can be reduced more than a case when a lens body with a small diameter is used.

The thickness of the lens body may be set in accordance with a desired refractive index and the like. The lens body is constituted by a soft material which makes the lens body foldable. The term "foldable" stated herein is used with a meaning that the intraocular lens including the lens body can be folded at least in half. Therefore, the soft material constituting the lens body is the material having a high flexibility to the extent that the lens body can be folded. Specifically, for example, the soft material such as silicon resin, acrylic resin, hydrogel or urethane resin may be used.

2-2. Support Portion

As long as the support portions of the present embodiment can support the lens body in the crystal lens capsule, the number, the shape, the material and the like of the support portions are not specifically limited, and the support portions may extend arm-like from the lens body, and may be a plate shape or a closed loop shape, but the following may be mentioned as an example.

The support portions of the present embodiment are formed so as to extend outward from the outer peripheral portion of the lens body. The support portions are the portions that support the lens body when the intraocular lens is inserted into an eye. The two support portions are formed in one intraocular lens. Each of the support portions extend from the portions where an axial line passing through the center C of the lens body intersects the peripheral edge of the lens body so as to draw a circular arc in a counterclockwise direction of the respective drawings.

2-3. Modified Examples and Preferable Examples Relating to the Intraocular Lens

The intraocular lens of the present embodiment is not limited to the aforementioned embodiments, but includes various modifications and improvements within the scope of deriving specific effects obtained by the constituent features of the invention and combinations thereof.

(Presence or Absence of the Support Portions)

The intraocular lens of the present embodiment includes the lens body and the support portions, but another member may also have a function of supporting the lens body in the crystal lens capsule, which is the function of the support portions. For example, it is also acceptable that the lens body of the present embodiment is placed on a structure having a shape conforming to the crystal lens capsule, and inserted together into the crystal lens capsule.

However, the intraocular lens is easily folded in the present embodiment, thus, it is preferable that the intraocular lens having the support portions is folded in an injector and inserted into the crystal lens capsule.

Note that, if the support portions in this case are integral type with the lens body (so-called one piece type), it is possible to sufficiently exhibit the effect of facilitating fold of the intraocular lens. However, the present invention is not limited thereto, for example, and it is also acceptable to employ the support portions of a separate type with the lens body.

(Sag Average Value)

The sag values of the back surface and the front surface of the lens body of the present embodiment are respectively defined, and the sag values which satisfy the aforementioned definition are obtained at all points in the back surface and the front surface.

On the other hand, according to the examination by the present inventor, it is clear that the effect of the present invention is exhibited at all points in the back surface and the front surface, even if the aforementioned definition is not satisfied.

Specifically, it is clear that the effect of the present invention (i.e., the suppression of the entry of the migratory cells and facilitating fold of the lens) is exhibited by satisfying the aforementioned definition, after replacing the "sag value" defined as described above, with the "sag average value"

(Condition 2)

In the back surface, a sag average value of the back surface in the region within a predetermined distance from an optical center Cp is not more than a sag average value of a virtual spherical surface Sp in the region $\alpha p$ within the predetermined distance from the optical center Cp, and the sag average value of the back surface in the region $\beta p$ outside of the predetermined distance from the optical center Cp becomes larger than the sag average value of the virtual spherical surface Sp in the region $\beta p$ outside of the predetermined distance from the optical center Cp, and in the front surface, a sag average value of the front surface in a region in a predetermined distance from an optical center Ca is not less than a sag average value of a virtual spherical surface Sa in the region $\alpha a$ within the predetermined distance from the optical center Ca, and the sag average value of the front surface in the region $\beta a$ outside of the within the predetermined distance from the optical center Ca becomes smaller than the sag average value of the virtual spherical surface Sa in the region $\beta a$ outside of the the predetermined distance from the optical center Ca.

Here, the sag average value of the back surface or the virtual spherical surface Sp is the average value of the sag value at each point inside or outside of the region within the predetermined distance from the optical center Cp. Moreover, the sag average value of the front surface or the virtual spherical surface Sa is the average value of the sag value at each point inside or outside of the region within the predetermined distance from the optical center Ca.

For example, when the sag value of the back surface or the front surface is measured at a predetermined number of measurement points equally spaced from each other (for example in a grid shape), the aforementioned definition is not satisfied at several points, and the difference between the sag value of the virtual spherical surface Sp and the sag value of the back surface is small even if the aforementioned definition is not satisfied, and if the aforementioned definition is satisfied at the other points, the back surface can be sufficiently protruded. This is also applied to the front surface, and when the aforementioned specification is not satisfied at several points, and the difference between the sag value of the virtual spherical surface Sa and the sag value of the front surface is small, and when the aforementioned definition is satisfied at the other points, the front surface has a shape which follows the definition even if the back surface protrudes, thus, it is possible to facilitate fold of the lens body or the intraocular lens, because even if the back surface is protruded, the front surface follows the protruded shape of the back surface.

(Substantial Sag)

In addition to the sag average value, according to the examinations by the present inventor, when the sag values of the back surface and the front surface are measured at a predetermined number of measurement points equally spaced from each other, and if there are half or more measurement points which satisfy Condition 1 regarding the aforementioned back surface and the front surface, inside and outside of the region of a predetermined distance in the rear surface and the front surface (hereinafter, referred to as Condition 3), it is clear that the effect of the present invention (i.e., the suppression of entry of the migratory cells and facilitating fold of the lens) is exhibited.

For example, when the sag value of the back surface or the front surface is measured at a predetermined number of measurement points equally spaced from each other (for example in a grid shape), and when the aforementioned definition is not satisfied at several points, and the aforementioned definition is satisfied at the other points, the effect of the present invention is sufficiently exhibited in the same manner as stated for the sag average value mentioned earlier. Further, the measurement points satisfying Condition 1 are preferably 80% or more of entire the measurement points, more preferably 90% or more, and even more preferably 95% or more.

Note that, it is sufficient to satisfy at least one of the conditions of the sag value (Condition 1) given in the present embodiment, and the sag average value (Condition 2) given above, and the substantial sag (Condition 3). It is also acceptable to satisfy a plurality of these conditions.

(Deviation of the Peripheral Edge from the Virtual Spherical Surface)

It is also possible to define the differences of the shapes with the virtual spherical surface by the following expressions other than the sag value.

Peripheral edge Ep of the back surface is separated by 0.1 mm or more from peripheral position Eps of the virtual spherical surface Sp in a direction vertical to a tangent plane at the optical center Cp, namely, in a direction from the back surface to the front surface, the peripheral position Eps being located at a distance of the peripheral edge Ep of the back surface from the optical center Cp on the tangent plane.

Peripheral edge Ea of the front surface is separated by 0.1 mm or more from peripheral position Eas of the virtual spherical surface Sa in a direction vertical to a tangent plane at the optical center Ca, namely, in a direction from the back surface to the front surface, the peripheral position Eas being located at a distance of the peripheral edge Ea of the front surface from the optical center Ca on the tangent plane.

It is preferable to satisfy the aforementioned definition, because the shape of the lens body can be expressed more clearly, the optical part of the back surface can be sufficiently protruded with respect to the peripheral edge of the back surface and the thickness of the lens body can be appropriate to facilitate fold of the lens.

Note that, the peripheral edge of the back surface may be provided with an acute angle. The posterior capsule is stretched by the center portion of the back surface which makes it difficult for the migratory cells to enter, but since the peripheral edge of the back surface is provided with the acute angle, it is possible to reduce the probability of migrating cells entering the gap between the back surface and the posterior capsule.

(Effective Optical Portion)

In the present embodiment, there are no limitations regarding which portion of the lens body exhibits the optical function in accordance with the prescription. For example, the optical function in accordance with the prescription may be exhibited in the entire the lens body.

Conversely, the optical function may be exhibited only in a predetermined portion of the lens body. This portion is referred to as an effective optical portion. For example, the back surface and the front surface of the lens body may respectively adopt a configuration including an effective optical portion which exhibits the optical function in accordance with the prescription and a peripheral portion disposed around the effective optical portion.

In this case, the peripheral portion is shaped in such a way as to protrude, in order to dispose an effective optical portion which is a central portion on a flat surface of the truncated cone, not only for exhibiting the optical function to realize the prescription. However, it does not matter if the effective optical portion has a shape for suppressing an astigmatism which occurs in the peripheral portion.

Note that, the effective optical portion stated herein and the abovementioned central portion may or may not completely match with each other as a region.

(Spherical and Aspherical)

The shape of the lens body of the present embodiment is not specifically limited, and the front surface, the back surface, or both surfaces may be spherical, aspheric, or a combination thereof.

(Monofocal and the Like)

Further, the front surface, the back surface, or both surfaces of the lens body have a shape which is at least one of monofocal, bifocal or multifocal, or toric, the bifocal and the multifocal being refractive, diffractive, or a combination thereof. Further, a surface having a step or a Fresnel surface may be used in a part or an entire part of the configuration.

3. EFFECT OF THE EMBODIMENT

According to the present embodiment, the following effects can be obtained, in addition to the effects listed above.

To restate, first, when the intraocular lens is inserted into the crystal lens capsule, the center portion in the back surface protrudes so as to become a plateau surface, thus, the posterior capsule is stretched by the center portion and the center portion is strongly pressed against the posterior capsule. As a result, the entry of the migratory cells between the posterior capsule and the lens body can be effectively suppressed, and thus, the occurrence of a secondary cataract can be suppressed. Due to the occurrence of the aforementioned stretching to the posterior capsule by the center portion, wrinkles and streaks are less likely to occur in the posterior capsule. These wrinkles and streaks may become the cause of optical failure (glare and the like), thus, it is useful to make it difficult for these to occur.

Further, due to the occurrence of the aforementioned stretching, the intraocular lens is fixed in the capsule, and, it is possible to suppress the movement, tilting, eccentricity (deviation and offset) and the like of the intraocular lens.

Further, according to the present embodiment, the peripheral edge of the lens body can be easily wrapped in the posterior capsule. The later the time that the intraocular lens is wrapped in the posterior capsule, the longer the time that the gap exists between the back surface of the lens body and the posterior capsule, and thus, the probability of entry of the migratory cells increases. However, in the present embodiment, the posterior capsule is stretched mainly at the center portion, thus, it is relatively easy for the peripheral portion to contact with the posterior capsule. As a result, the occurrence of the secondary cataract can be suppressed.

Due to the occurrence of the aforementioned stretching, the time required for a contact between the back surface of the intraocular lens and the posterior capsule can be certainly reduced. As a result, the occurrence of the secondary cataract can be suppressed.

Each of the aforementioned effects is exhibited by making the gap between the back surface of the intraocular lens (the lens body) and the posterior capsule as small as possible, and by making the space for the gap as small as possible. In other words, the contact area between the back surface of the lens body and the posterior capsule is made as large as possible.

Further, the intraocular lens of the present embodiment is particularly effective for a toric lens, because it is predicted that rotation of the postoperative intraocular lens (IOL) can be decreased, and intracapsular stability can be improved.

Further, facilitating fold of the intraocular lens is provided as a subject of the present invention, but according to the present embodiment, the back surface protrudes in a shape of a truncated cone, while the front surface is changed in design so as to be in the case of any of (i) to (iii) (i.e., the rate of rise of the protrusion of the front surface is smaller or recessed than the rate of rise of the protrusion of the back surface). Therefore, the lens body can be made relatively thin, and it is possible to fold the intraocular lens relatively easily. Specifically, when the intraocular lens of the present embodiment is one piece type, it is possible to facilitate a folding operation even in a case that the support portion is folded and wrapped in the lens body.

As described above, according to the present embodiment, the intraocular lens is provided, which improves intracapsular stability and suppresses the occurrence of the secondary cataract while facilitating fold of the intraocular lens.

4. MODIFICATION EXAMPLES

The technical scope of the present invention is not limited to the aforementioned embodiments, but includes various modifications and improvements within the scope of deriving specific effects obtained by the constituent features of the invention and combinations thereof.

(Applications Other than Insertion into the Crystal Lens Capsule)

The intraocular lens of the present embodiment is based on the insertion into the crystal lens capsule (in the bag), but is not limited to this application. For example, the intraocular lens of the present embodiment is also useful in the case of an out the bag application in which the intraocular lens is disposed outside of the crystal lens capsule and between the iris and the crystal lens capsule. The reason therefore is that the back surface of the lens body in the intraocular lens of the present embodiment is shaped in such a way as to protrude to the retinal side, and the front surface is disposed relatively close to the retina. With this shape, it is possible to reduce the chance of contact with the iris present on the corneal side of the intraocular lens.

(Definition 1 of Shape of the Lens Body)

In addition to the definition using the sag value as stated above, it is also possible to define the shapes of the back surface and the front surface, particularly the protrusion shape of the back surface as follows.

"An intraocular lens including a lens body having two opposing surfaces A and B, wherein the entire surface A has a shape protruding in a shape of a truncated cone from a peripheral edge of the surface A and the entire surface B has a shape which is recessed from a peripheral edge of surface B toward one of the optical axis directions."

In the aforementioned definition, in consideration of the applications other than insertion into the crystal lens capsule, the positional relationship between the front surface, the back surface, the anterior capsule, and the posterior capsule is not defined.

In the surface A which corresponds to the back surface of the lens body of the present embodiment, the entire back surface protrudes with respect to the peripheral edge. However, the shape at this time is a truncated cone-shape. In short, the central portion corresponds to the plateau surface of the truncated cone, and the peripheral portion corresponds to a portion of the truncated cone. The connection portion described above is present at the boundary between the central portion and the peripheral portion. The connection portion and the position thereof are as stated in the present embodiment.

Further, in the surface B which corresponds to the front surface of the lens body of the present embodiment, contrary to the surface A, the entire surface B has a recessed shape with respect to the peripheral edge of the surface B. Here, the term "recessed" indicates that the surface B is disposed at a position recessed from the plane formed by the peripheral edge of the surface B. However, the vertex of the surface B may be present on the plane.

Note that, with regards to the surface B, the definition regarding the front surface in the above described Condition 1 may be adopted.

(Definition 2 of the Shape of the Lens Body)

The following is given as another definition.

"An intraocular lens including a lens body having a front surface disposed on a corneal side and a back surface disposed on a retinal side, wherein, the lens body, viewed from a peripheral edge of the lens body, has a shape which is bent toward the retinal side in a direction of an optical axis."

The aforementioned definition is different than specification 1, and defines an arrangement relationship between the back surface and the front surface when the intraocular lens is inserted into the eye. On the other hand, the expression "bent" is used as the shape of the back surface. This shows a state in which a region closer to the center than the peripheral edge of the back surface is disposed on the retinal side (rearward) compared to the peripheral edge of the back surface (in short, a state in which the peripheral edge is disposed closest to the corneal side in the back surface, for example, as illustrated in FIG. 3(b), FIG. 6(b) and FIG. 7(b)). On the other hand, the front surface may be in a state in which the region closer to the center than the peripheral edge of the front surface is disposed on the retinal side (rearward) compared to the peripheral edge of the front surface (in short, a state in which the peripheral edge is disposed closest to the corneal side in the back surface, for example, as illustrated in FIG. 3(b) and FIG. 6(b)), or, in a state in which the above region exists on the same plane as a plane formed by the peripheral edge of the front surface. Of course, it is preferable that an entire front surface is disposed on the retinal side (rearward) compared to the peripheral edge of the front surface. This is because the lens body can be made thin, and fold of the lens can be further facilitated.

Note that, regarding the front surface, the definition regarding the front surface in the above described Condition 1 may be adopted.

(Definition 3 of the Shape of the Lens Body)

The aforementioned definition: "satisfies at least one of Conditions 1 to 3" is given as a specific example, but it is also possible to regard this definition itself as an invention which is not dependent upon the cases (i) to (iii). Even in this case, the effect of the present invention is exhibited as described in detail in the present embodiment.

LIST OF REFERENCE SIGNS

1 . . . Intraocular lens
2 . . . Lens body
3 . . . Support portion
100 . . . Intraocular lens
200 . . . Lens body
300 . . . Support portion
Cp . . . Optical center of back surface
Sp . . . Virtual spherical surface of back surface
Rcp . . . Curvature radius of virtual spherical surface Sp
Ep . . . Peripheral position of back surface
Eps . . . Peripheral position of virtual spherical surface Sp
αp . . . Center portion of back surface
βp . . . Peripheral portion of back surface
Ca . . . Optical center of front surface
Sa . . . Virtual spherical surface of front surface
Rca . . . Curvature radius of virtual spherical surface Sa
Ea . . . Peripheral position of front surface
Eas . . . Peripheral position of virtual spherical surface Sa
αa . . . Center portion of front surface
βa . . . Peripheral portion of front surface

The invention claimed is:

1. An intraocular lens for use in an eye including a lens capsule with an anterior capsule and a posterior capsule, the intraocular lens comprising:
a lens body having a back surface with a peripheral edge and an optical center Cp, a front surface with a peripheral edge and an optical center Ca, and an optical axis Ca-Cp defining a front to back direction;
the back surface, from the back surface peripheral edge to the back surface optical center Cp, being shaped in such a way as to extend toward the back surface optical center in the front to back direction of the optical axis Ca-Cp and a peripheral portion cross-section has a truncated cone shape, and
the front surface, from the front surface peripheral edge to the front surface optical center Ca, being shaped in such a way as to extend toward the front surface optical center in the front to back direction of the optical axis Ca-Cp; and
means for supporting the lens body within the lens capsule such that the back surface contacts the posterior capsule;
wherein
a peripheral position Ep of the back surface is separated by 0.1 mm or more from a peripheral position Eps of the virtual spherical surface Sp in a direction vertical to a tangent plane at the optical center Cp, namely, in a direction from the back surface to the front surface, the peripheral position Eps being located at a distance of a peripheral edge Ep of the back surface from the optical center Cp on the tangent plane, and
a peripheral position Ea of the front surface is separated by 0.1 mm or more from a peripheral position Eas of the virtual spherical surface Sa in a direction vertical to a tangent plane at the optical center Ca, namely, in a direction from the back surface to the front surface, the peripheral position Eas being located at a distance of a peripheral edge Ea of the front surface from the optical center Ca on the tangent plane.

2. The intraocular lens according to claim 1, wherein the distance from the peripheral position Ep of the back surface to the peripheral position Ea of the front surface is less than the distance from the peripheral position Eas of the virtual spherical surface Sa to the peripheral position Ea of the front surface.

3. The intraocular lens according to claim 2, wherein at least one of the following conditions is satisfied
Condition 1
in the back surface, a sag value of the back surface at a peripheral region is greater than a sag value of the virtual spherical surface Sp at the peripheral region, and
in the front surface, a sag value of the front surface at a peripheral region is less than a sag value of the virtual spherical surface Sa at the peripheral region,
Condition 2
in the back surface, a sag average value of the back surface in a peripheral region is greater than a sag average value of the virtual spherical surface Sp in the peripheral region, and
in the front surface, a sag average value of the front surface in a peripheral region is less than a sag average value of the virtual spherical surface Sa in the peripheral region,
Condition 3
in the back surface and the front surface, when the sag values at peripheral regions thereof are measured at a predetermined number of measurement points equally spaced from each other, there are half or more measurement points which satisfy Condition 1,
wherein the sag value of the virtual spherical surface is a vertical distance from a tangent plane at the optical center, to the virtual spherical surface,
the sag average value of the back surface or the virtual spherical surface Sp is the average value of the sag value at each point at peripheral region within the predetermined distance from the optical center Cp, and
the sag average value of the front surface or the virtual spherical surface Sa is the average value of the sag value at each at peripheral region within the predetermined distance from the optical center Ca.

4. The intraocular lens according to claim 3, wherein the curvature of the back surface at the peripheral region is greater than the curvature of the back surface at the center region.

5. The intraocular lens according to claim 4, wherein the cross section area of the back surface of the lens body, that is the area of the lens body between a plane at the peripheral position Ep of the back surface which is perpendicular to the optical axis Ca-Cp and a tangent plane at the optical center Cp of the back surface, is wider than the cross section area of the front surface of lens body, that is the area of the lens body between a plane at peripheral position Ea of the front surface which is perpendicular to the optical axis Ca-Cp and a tangent plane at the optical center Ca of the front surface.

6. The intraocular lens according to claim 5, wherein an optical function in accordance with a prescription is exhibited in an entire lens body.

7. The intraocular lens according to claim 5, wherein the back surface and the front surface of the lens body respectively include an effective optical portion which exhibits an optical function in accordance with a prescription and the peripheral portion disposed around the effective optical portion.

8. The intraocular lens according to claim 5, wherein the front surface, the back surface, or both surfaces of the lens body is spherical, aspheric, ora combination thereof.

9. The intraocular lens according to claim 5, wherein
at least one of the front surface or the rear surface has a shape selected from the group consisting of monofocal, bifocal, multifocal and toric,
the bifocal shape is at least one of refractive or diffractive, and
the multifocal shape is at least one of refractive or diffractive.

10. The intraocular lens according to claim 1, wherein at least one of the following conditions is satisfied
Condition 1
in the back surface, a sag value of the back surface at a peripheral region is greater than a sag value of the virtual spherical surface Sp at the peripheral region, and
in the front surface, a sag value of the front surface at a peripheral region is less than a sag value of the virtual spherical surface Sa at the peripheral region,
Condition 2
in the back surface, a sag average value of the back surface in a peripheral region is greater than a sag average value of the virtual spherical surface Sp in the peripheral region, and
in the front surface, a sag average value of the front surface in a peripheral region is less than a sag average value of the virtual spherical surface Sa in the peripheral region,
Condition 3
in the back surface and the front surface, when the sag values at peripheral regions thereof are measured at a predetermined number of measurement points equally spaced from each other, there are half or more measurement points which satisfy Condition 1,
wherein the sag value of the virtual spherical surface is a vertical distance from a tangent plane at the optical center, to the virtual spherical surface,
the sag average value of the back surface or the virtual spherical surface Sp is the average value of the sag value at each point at peripheral region within the predetermined distance from the optical center Cp, and
the sag average value of the front surface or the virtual spherical surface Sa is the average value of the sag value at each at peripheral region within the predetermined distance from the optical center Ca.

11. The intraocular lens according to claim 10, wherein the curvature of the back surface at the peripheral region is greater than the curvature of the back surface at the center region.

12. The intraocular lens according to claim 11, wherein the cross section area of the back surface of the lens body, that is the area of the lens body between a plane at the peripheral position Ep of the back surface which is perpendicular to the optical axis Ca-Cp and a tangent plane at the optical center Cp of the back surface, is wider than the cross section area of the front surface of lens body, that is the area of the lens body between a plane at peripheral position Ea of the front surface which is perpendicular to the optical axis Ca-Cp and a tangent plane at the optical center Ca of the front surface.

13. The intraocular lens according to claim 12, wherein an optical function in accordance with a prescription is exhibited in an entire lens body.

14. The intraocular lens according to claim 12, wherein the back surface and the front surface of the lens body respectively include an effective optical portion which exhibits an optical function in accordance with a prescription and the peripheral portion disposed around the effective optical portion.

15. The intraocular lens according to claim 12, wherein the front surface, the back surface, or both surfaces of the lens body is spherical, aspheric, or a combination thereof.

16. The intraocular lens according to claim 12, wherein
at least one of the front surface or the rear surface has a shape selected from the group consisting of monofocal, bifocal, multifocal and toric,
the bifocal shape is at least one of refractive or diffractive, and
the multifocal shape is at least one of refractive or diffractive.

* * * * *